(12) United States Patent
Alaparthi et al.

(10) Patent No.: US 10,957,140 B2
(45) Date of Patent: Mar. 23, 2021

(54) MULTI-FACTOR BIOMETRIC AUTHENTICATION

(71) Applicant: Intel Corporation, Santa Clara, CA (US)

(72) Inventors: Phani K. Alaparthi, Benguluru (IN); Tarakesava Reddy K, Bangalore (IN); Ovais F. Pir, Srinagar (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 16/236,025

(22) Filed: Dec. 28, 2018

(65) Prior Publication Data
US 2019/0139341 A1    May 9, 2019

(51) Int. Cl.
*G07C 9/37* (2020.01)
*A61B 5/1172* (2016.01)
*A61B 5/024* (2006.01)
*G08B 7/06* (2006.01)
*G07C 9/00* (2020.01)

(52) U.S. Cl.
CPC ............ *G07C 9/37* (2020.01); *A61B 5/02433* (2013.01); *A61B 5/02444* (2013.01); *A61B 5/1172* (2013.01); *G07C 9/00563* (2013.01); *G08B 7/06* (2013.01); *A61B 2560/0228* (2013.01)

(58) Field of Classification Search
CPC ... A61B 5/02444; A61B 5/1172; G06F 21/32; G06F 21/31; H04L 63/0861; H04L 2463/082; H04L 63/08; H04W 12/06
See application file for complete search history.

(56) References Cited

U.S. PATENT DOCUMENTS

| | | | |
|---|---|---|---|
| 8,902,045 B1 * | 12/2014 | Linn | G06F 21/32 340/5.53 |
| 10,360,367 B1 * | 7/2019 | Mossoba | H04L 63/0853 |
| 2015/0112452 A1 * | 4/2015 | He | A61B 5/742 700/11 |
| 2016/0308859 A1 * | 10/2016 | Barry | G07C 9/22 |
| 2016/0359827 A1 * | 12/2016 | Krishnaiah | G06F 21/31 |
| 2018/0293367 A1 * | 10/2018 | Urman | H04L 67/12 |
| 2018/0309792 A1 * | 10/2018 | Obaidi | H04L 63/0861 |
| 2019/0149334 A1 * | 5/2019 | Van Der Velden | H04L 9/0891 713/185 |

* cited by examiner

*Primary Examiner* — Mirza F Alam
(74) *Attorney, Agent, or Firm* — Hanley, Flight & Zimmerman, LLC

(57) ABSTRACT

Technology for an electronic device is described. The electronic device can include a fingerprint sensor, a heart rate sensor, and a controller. The controller can receive a fingerprint of a user captured using the fingerprint sensor. The controller can determine whether the fingerprint of the user matches a predefined fingerprint stored in a data store of the electronic device. The controller can receive heart rate information of the user captured using the heart rate sensor. The controller can determine whether the heart rate information is within a defined range. The controller can unlock the electronic device to allow the user to access the electronic device when the fingerprint of the user matches the predefined fingerprint stored in the data store and the heart rate information is within the defined range.

28 Claims, 6 Drawing Sheets

MULTI-FACTOR BIOMETRIC AUTHENTICATION

BACKGROUND

Device security or mobile device security has become an increasingly important aspect in mobile and personal computing. One particular concern is the security of personal and business information stored on mobile devices and other personal computing devices. To prevent unauthorized access to devices, a number of security measures can be incorporated into the device. For example, a device user can set a password or personal identification number (PIN) that is to be correctly entered in order to gain access to the device. If an unauthorized person gains possession of the device, most attempts of the unauthorized person to gain access to the device can be thwarted due to the device being password or PIN protected. Similarly, some devices include components that allow biometric identification of a user (e.g. via a finger print or facial recognition). In some cases, the user can enter their fingerprint in order to gain access to the device. When the device is fingerprint-protected, unauthorized persons can have difficulty gaining access to the device, thereby protecting data that is stored on the device.

BRIEF DESCRIPTION OF THE DRAWINGS

Features and advantages of technology embodiments will be apparent from the detailed description which follows, taken in conjunction with the accompanying drawings, which together illustrate, by way of example, various technology features; and, wherein.

Figure 1:
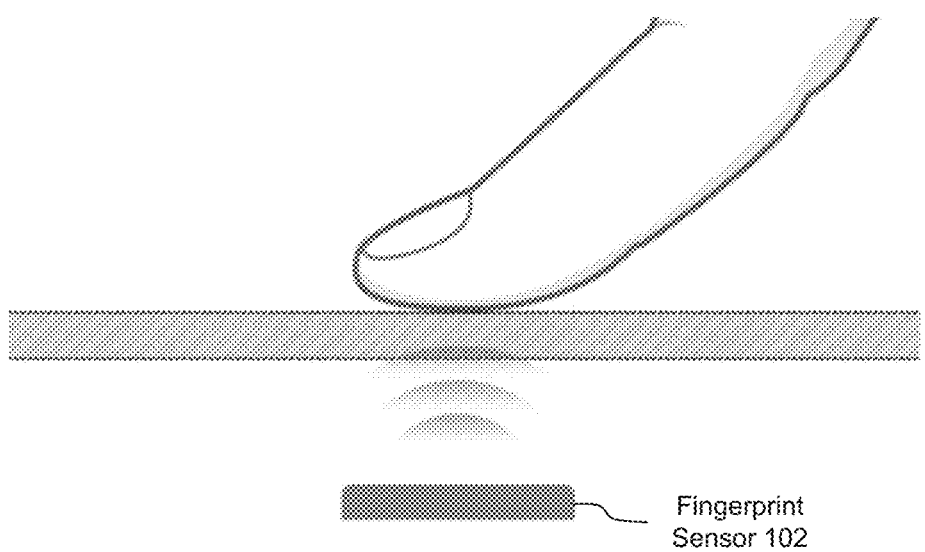
FIG. 1 illustrates detecting a fingerprint using a fingerprint sensor in accordance with an example embodiment.

Reference will now be made to the exemplary embodiments illustrated, and specific language will be used herein to describe the same. It will nevertheless be understood that no limitation on technology scope is thereby intended.

DESCRIPTION OF EMBODIMENTS

Before the disclosed technology embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various technology embodiments. One skilled in the relevant art will recognize, however, that such detailed embodiments do not limit the overall technological concepts articulated herein, but are merely representative thereof.

As used in this written description, the singular forms "a," "an" and "the" include express support for plural referents unless the context clearly dictates otherwise. Thus, for example, reference to "a bit line" includes a plurality of such bit lines.

Reference throughout this specification to "an example" means that a particular feature, structure, or characteristic described in connection with the example is included in at least one embodiment of the present invention. Thus, appearances of the phrases "in an example" or "an embodiment" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention can be referred to herein along with alternatives for the various components thereof. It is understood that such embodiments, examples, and alternatives are not to be construed as defacto equivalents of one another, but are to be considered as separate and autonomous representations under the present disclosure.

Furthermore, the described features, structures, or characteristics can be combined in any suitable manner in one or more embodiments. In the following description, numerous specific details are provided, such as examples of layouts, distances, network examples, etc., to provide a thorough understanding of invention embodiments. One skilled in the relevant art will recognize, however, that the technology can be practiced without one or more of the specific details, or with other methods, components, layouts, etc. In other instances, well-known structures, materials, or operations may not be shown or described in detail to avoid obscuring aspects of the disclosure.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in this written description, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," "maximized," "minimized," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a sensor with increased sensitivity can be different from other sensors (e.g. in a sensor array) in ways that give it a comparatively lower limited of detection. Thus, it may be able to detect events and gather information that is outside the capacity of the other sensors. A number of factors can cause such increased sensitivity, including materials, design, fabrication process, etc.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

Numerical amounts and data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

An initial overview of technology embodiments is provided below and then specific technology embodiments are described in further detail later. This initial summary is intended to aid readers in understanding the technology more quickly, but is not intended to identify key or essential technological features nor is it intended to limit the scope of the claimed subject matter. Unless defined otherwise, all technical and scientific terms used herein have the same meaning as commonly understood by one of ordinary skill in the art to which this disclosure belongs.

Fingerprint technology is increasingly used to secure electronic devices. Since fingerprints are unique between humans, a fingerprint sensor can be installed on an electronic device and used to securely allow/deny access to the electronic device. When an electronic device that is protected using fingerprint technology is stolen, it can be difficult for a perpetrator to gain access to the electronic device without the correct fingerprint. Thus, fingerprint technology can provide increased levels of security and an enhanced authentication experience for a user.

However, while fingerprint sensors can be an effective mechanism for locking and unlocking an electronic device under many circumstances, securing an electronic device using only fingerprint technology can suffer from several disadvantages. For example, a person that wishes to secretly gain access to an electronic device can guide an electronic device user's finger on the fingerprint sensor when the user is sleeping or unconscious or not awake, thereby deceitfully obtaining access to the electronic device. Further, in this case, there can be no trace or history of the fraudulent electronic device unlocking, so the user may not know that their electronic device was hacked while sleeping or unconscious or not awake. In another example, a person that wishes to secretly gain access to an unattended electronic device can create a fingerprint impression and use the fingerprint impression to deceitfully obtain access to the electronic device. Similarly, in this case, there can be no trace or history of the fraudulent electronic device unlocking, so the user may not know that their electronic device was hacked while unattended.

Some previous mechanisms for unlocking electronic devices also suffer from various drawbacks. For example, a face recognition system can allow biometric authentication for unlocking an electronic device. In this system, a dot projector module projects a grid of infrared dots onto a user's face, and an infrared camera module reads a resulting pattern and generates a three dimensional facial map, which is compared to a registered face and the user can be authenticated when the two faces match sufficiently. However, one drawback is that the user must look directly at the electronic device to unlock the electronic device, and a front camera must be turned on for unlocking the electronic device. In another example, a pattern unlock mechanism can be used for unlocking an electronic device. In this mechanism, a user can draw a pattern on an on-screen grid of dots, and if the pattern matches a pattern set defined by the user, then the electronic device can become unlocked. However, using photographs taken under a variety of lighting and camera positions, it is sometimes possible to determine a full or partial pattern for an electronic device, which can then be used to hack into the electronic device.

In the present technology, a user of an electronic device can be detected by measuring a time interval between two heart beats (or a heart rate) along with fingerprint sensing, which can be used to determine whether the user is awake or conscious. In other words, a combination of heart rate monitoring and fingerprint matching can be used for unlocking an electronic device. Generally, a heartbeat interval time of a sleeping or unconscious user is not the same as when the same user is awake or conscious. For example, a user's heartbeat interval (or heart rate) when asleep can be approximately 30% less than the same user's heartbeat interval when the user is awake. Therefore, in addition to checking for a fingerprint match when unlocking an electronic device, a user's heartbeat interval can be detected to verify that the user is awake or conscious. When there is a fingerprint match and the user is determined as being awake or conscious (based on the heartbeat interval), an electronic device can be unlocked. As a result, increased security can be provided to users when they are sleeping or in an unconscious state.

Furthermore, using a combination of heart rate monitoring and fingerprint matching can serve to distinguish between human touch versus a fake fingerprint or fingerprint impression, as a material used for creating the fingerprint impression can have different photo characteristics as compared to human skin.

In a previous solution, with a fingerprint sensor only implementation, when a user touched the fingerprint sensor, the fingerprint sensor detected a fingerprint of the user and determined whether the detected fingerprint matched with an authenticated user's fingerprint. When there was a match, an electronic device would be unlocked. However, one drawback with this previous solution is that there was no analysis of whether the user was sleeping (or unconscious) or awake (or conscious). Thus, a perpetrator could use the fingerprint of an authenticated user to unlock the electronic device when the authenticated user was unconscious.

In the present technology, a heart rate monitor can be used in conjunction with a fingerprint sensor in order to unlock an electronic device. The heart rate monitor can include an infrared (IR) light emitting diode (LED) and a photo diode. The fingerprint sensor can determine whether a detected fingerprint matches with a stored fingerprint of an authenticated user. The heart rate monitor can detect a heartbeat interval (or heart rate) of the user. When the heartbeat interval is within a defined range or matches a stored reference heartbeat interval of the authenticated user, then a determination can be made that the user is awake or conscious. The stored reference heartbeat interval can indicate a typical heartbeat interval of the user when the user is awake. When there is both a fingerprint match and a determination that the user is awake or conscious, as indicated by the user's detected heartbeat interval, the electronic device can be unlocked.

In one example, a heartbeat can cause a variation in the flow of blood to different regions of the body. When a fingertip is placed over a sensor assembly that includes the heart rate monitor and the fingerprint sensor, the IR LED can transmit an infrared light into the fingertip, and a part of the infrared light can be reflected back from the blood inside the finger arteries. The amount of infrared light absorbed can depend on a blood volume inside the fingertip. Each time the heart beats, a pulse can be generated and an amount (e.g. a change in amount) of reflected infrared light can be detected by the photo diode. A time duration between pulses (e.g., a 3 to 4 pulse duration) can be determined and an average time interval between heartbeats can be calculated.

In one example, generally speaking for adults, a typical heartbeat for a user can be approximately 60 to 100 beats per minute (BPM) while the user is resting. While the same user is asleep, the user's heartbeat can slow down to approximately 40-48 BPM. In other words, a typical heartbeat of a user when asleep can be less (e.g., about 30% less) than a typical heartbeat of the same user when awake and resting. As a result, the user's heartbeat interval can increase by approximately 30% when the user is sleeping.

In one example, when a fingertip is placed over the fingerprint sensor, the fingerprint sensor can sense the fingerprint and the heart rate monitor (which includes the IR LED and the photo diode) can calculate a time interval between heartbeats to determine whether the user is awake or sleeping. When the time interval between heartbeats is increased (i.e., a reduced heart rate), the user can be considered asleep or unconscious, and the electronic device may not be unlocked, irrespective of whether there is a fingerprint match. On the other hand, when the time interval between heartbeats is decreased as compared to the time interval between heartbeats when the user is asleep or unconscious (i.e., an increased heart rate), the user can be considered awake or conscious, and the electronic device can be unlocked, when there is a fingerprint match.

In one example, a heartbeat interval can be calculated for a first condition, which corresponds to when a user is awake or conscious, as well as a second condition, which corresponds to when a user is sleeping or unconscious. For the first condition when the user is awake, a BPM can vary from 60-100. When the BPM is 100, the time interval between each heart beat is 60/100 or 0.6 seconds. When the BPM is 60, the time interval between each heart beat is 60/60 or 1 second. Thus, the time interval between heartbeats when the user is awake can vary from 0.6 seconds to 1 second. For the second condition when the user is sleeping, a BPM can be reduced to 40-48. When the BPM is 40, the time interval between each heartbeat is 60/40 or 1.5 seconds. When the BPM is 48, the time interval between each heartbeat is 60/48 or 1.25 seconds. Thus, the time interval between heartbeats when the user is sleeping can vary from 1.25 seconds to 1.5 seconds. Thus, there can be a 0.25 second variation when a user is awake as compared to when the user is sleeping (and in some cases more than 0.25 seconds). This difference in time interval between hearts when a user is asleep versus awake can be used to determine whether a detected heartbeat time interval (or time interval between heart beats) or a detected heart rate of a user indicates that the user is awake or not awake, and based on that determination along with a fingerprint match, an electronic device of the user can be unlocked.

FIG. 1 illustrates an example of detecting a fingerprint using a fingerprint sensor 102. The fingerprint sensor 102 can be included in or coupled to an electronic device (not shown). The fingerprint sensor 102 can be used to authenticate a user that is attempting to access the electronic device. For example, a user can place their finger on top of the fingerprint sensor 102. The fingerprint sensor 102 can detect the user's fingerprint. The user's detected fingerprint can be compared against a stored fingerprint of the user, and if there is a match, the user can be authenticated and allowed to access the electronic device.

Figure 2:
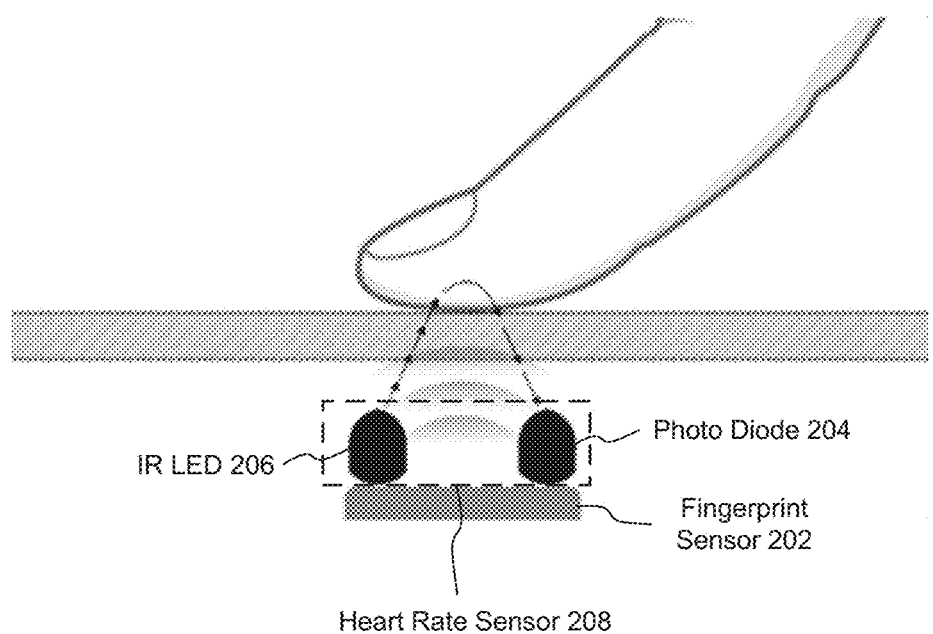
FIG. 2 illustrates detecting a fingerprint using a fingerprint sensor and detecting a heart rate using a heart rate sensor in accordance with an example embodiment.

FIG. 2 illustrates an example of detecting a fingerprint using a fingerprint sensor 202 and detecting a heart rate using a heart rate sensor 208. The heart rate sensor 208 can include an infrared (IR) light emitting diode (LED) 206 and a photo diode 204. The fingerprint sensor 202 and the heart rate sensor 208 can be included in a sensor assembly, and the sensor assembly can be included in or coupled to an electronic device (not shown). The fingerprint sensor 202 and the heart rate sensor 208 can be used to authenticate a user that is attempting to access the electronic device. For example, a user can place their finger on top of the sensor assembly, which includes the fingerprint sensor 202 and the heart rate sensor 208. The fingerprint sensor 202 can detect the user's fingerprint. The user's detected fingerprint can be compared against a stored fingerprint of the user, and a determination can be made as to whether there is a match between the user's detected fingerprint and the stored fingerprint of the user. In addition, the heart rate sensor 208 can detect the user's heartbeat interval (or heart rate). When the detected heartbeat interval is within a defined range or matches a stored reference heartbeat interval of the user, then a determination can be made that the user is awake or conscious. The stored reference heartbeat interval can indicate a typical heartbeat interval of the user when the user is awake. When there is both a fingerprint match and a determination that the user is awake or conscious, as indicated by the user's detected heartbeat interval, the electronic device can be unlocked.

Figure 3:
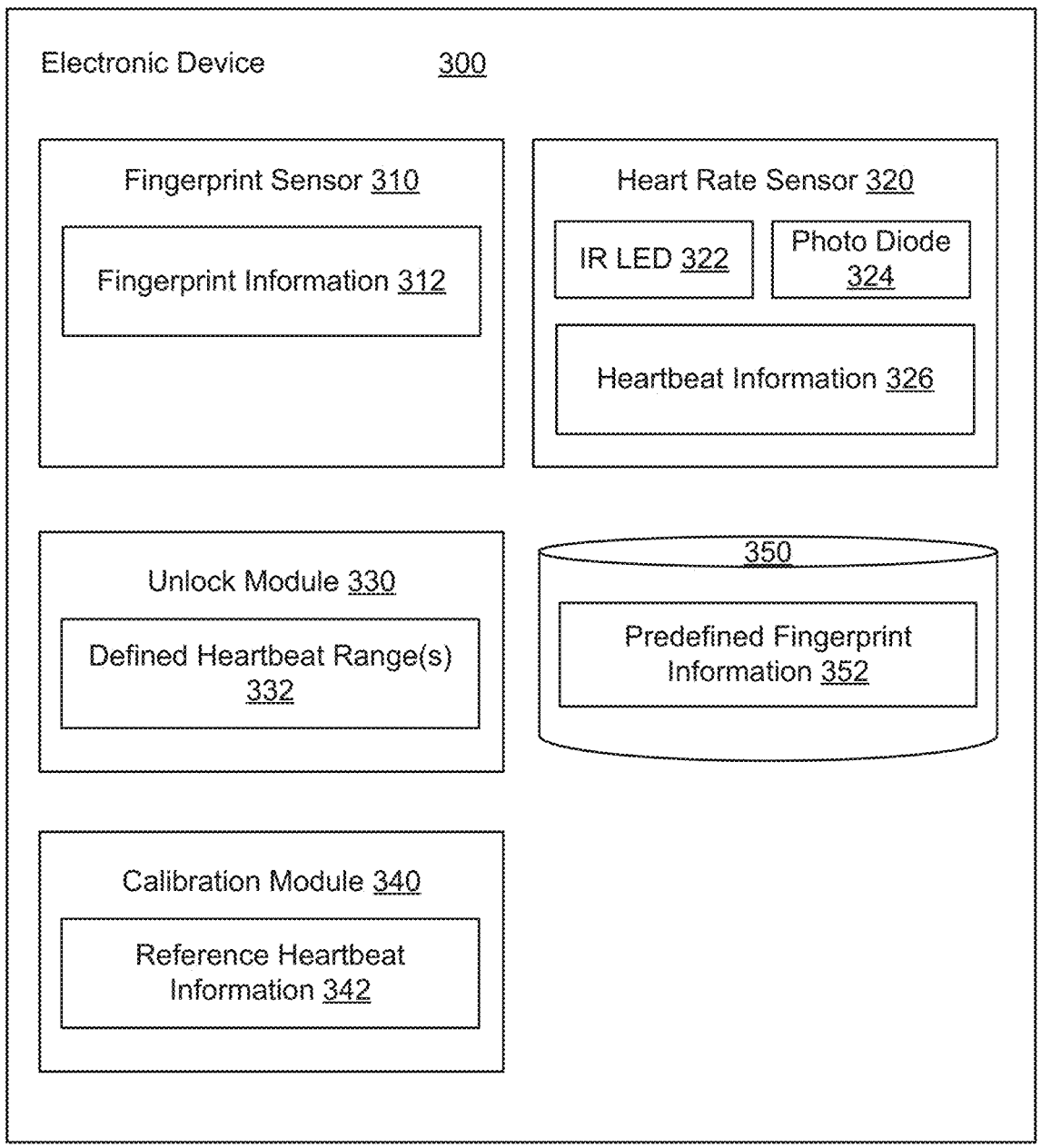
FIG. 3 illustrates an electronic device that is configured to unlock based on fingerprint information and heartbeat information in accordance with an example embodiment.

FIG. 3 illustrates an example of an electronic device 300 that is configured to unlock based on fingerprint information 312 and heartbeat information 326. The electronic device 300 can include a fingerprint sensor 310 operable to capture the fingerprint information 312 of a user that is attempting to access the electronic device 300. The electronic device 300 can include a heart rate sensor 320 operable to capture the heartbeat information 326 of the user that is attempting to access the electronic device 300. The heartbeat information 326 can include a heartbeat time interval of the user (i.e., a time interval between heart beats of the user) or a heart rate of the user (e.g., heart beats per minute, or BPM). The electronic device 300 can use both the fingerprint information 312 and heartbeat information 326 when determining whether to unlock the electronic device 300 for enhanced security.

While a number of different heart rate sensor types can be use, in one example, the heart rate sensor 320 can include an infrared (IR) light emitting diode (LED) 322 and a photo diode 324 for capturing the heartbeat information 326 of the user. For example, when a fingertip is placed over the heart rate sensor 320, the IR LED 322 can transmit an infrared light into the fingertip, and a part of the infrared light can be reflected back from the blood inside the finger arteries and detected by the photo diode 324. Each time the user's heart beats, a pulse can be generated and an amount of reflected infrared light can be detected by the photo diode 324. As a result, the IR LED 322 and the photo diode 324 in the heart rate sensor 320 can be used to capture the heartbeat information 326 of the user.

In one example, the electronic device 300 can include a mobile device, such as a smartphone, a tablet computer, a laptop computer, a portable memory device, etc. In another example, the electronic device 300 can include a desktop computer, a printer, a scanner, a fingerprint door lock, a television, or a household appliance such as a refrigerator, microwave, oven or washer/dryer. In yet another example, the electronic device could be a vehicle, such as a car. In short, nearly any device or system that can be secured with fingerprint identification can utilize the present technology.

In one configuration, the electronic device 300 can include an unlock module 330. The unlock module 330 can receive the fingerprint information 312 of the user captured using the fingerprint sensor 310. The unlock module 330 can determine whether the fingerprint information 312 matches predefined fingerprint information 352 stored in a data store 350 of the electronic device 300. For example, the user may have previously provided the predefined fingerprint information 352 for storage in the data store 350 during a setup or calibration process of the electronic device 300. The predefined fingerprint information 352 can serve as a reference to which subsequent fingerprint scans are compared in order to determine whether there is a match. The unlock module 330 can receive the heartbeat information 326 of the user captured using the heart rate sensor 320. The unlock module 330 can determine whether the heartbeat information 326 indicates that the user's heartbeat interval or heart rate is within a defined heartbeat range 332, which can indicate that the user is awake or conscious. The unlock, module 330 can determine to unlock the electronic device 300 to allow the user to access the electronic device 300 when the fingerprint information 312 of the user matches the predefined fingerprint information 352 stored in the data store 350 and the heartbeat information 326 indicates that the user's heartbeat interval or heart rate is within the defined heartbeat range 332.

In one example, the defined heartbeat range(s) 332 can include ranges that can indicate whether the user is awake or conscious. The defined heartbeat range(s) 332 can be applicable to a general population, or can be applicable to a specific subset of the population (e.g., male, female, age, level of physical fitness, ethnicity, etc.) The defined heartbeat range(s) 332 can include ranges for BPM or a heartbeat interval, which can be used to determine whether a user is awake or not awake. In one example, when the user's heart rate is within a range of 60-100 BPM, the user can be considered as being awake or conscious. In another example, when the user's heartbeat interval is within a range of 0.6 seconds to 1 second, the user can be considered as being awake or conscious. In another example, when the user's heart rate is lower than 48 BPM (e.g. within a range of 40-48 BPM), the user can be considered as being not awake or unconscious. In another example, when the user's heartbeat interval is within a range of 1.25 seconds to 1.5 seconds, the user can be considered as being not awake or unconscious.

In one configuration, the user can place their finger on a sensor assembly of the electronic device 300 that includes the fingerprint sensor 310 and the heart rate sensor 320 for a defined period of time (e.g., a few seconds) until the unlock module 330 determines to unlock the electronic device 300. When the user continues to place their finger on the sensor assembly of the electronic device 300 for an additional period of time (e.g., 2 seconds) after the electronic device 300 is unlocked, the electronic device 300 can send the heartbeat information 342 of the user to a defined group of users. For example, the defined group of users can include family members, friends, colleagues, etc.

In one configuration, the electronic device 300 can include a calibration module 340. During an initial setup or calibration of the electronic device 300, the user can enter reference heartbeat information 342 or the electronic device 300 can detect reference heartbeat information 342 for the user. The reference heartbeat information 342 can include a reference heartbeat interval or reference heart rate of the user when the user is awake or conscious. The reference heartbeat information 342 can be specific for a particular user, since it is possible that different users can have different heartbeat intervals or heart rates when awake and resting. For example, a well-trained athlete can have a resting BPM of 40, which would be reflected in reference heartbeat information 342 of that athlete.

In one example, the calibration module 340 can receive updated reference heart rate information of the user during a recalibration period. The updated reference heart rate information can indicate an updated reference heartbeat interval or updated reference heart rate of the user when the user is awake or conscious. For example, over a period of time, the user may have dramatically improved in physical fitness and a resting heart rate of the user decreased. Therefore, the reference heartbeat information 342 of the user can constantly be updated over time to reflect a current level of physical fitness of the user.

In one configuration, the unlock module 330 can receive the heartbeat information 326 of the user captured using the heart rate sensor 320. The unlock module 330 can compare the heartbeat information 326 received from the heart rate sensor 320 with the reference heartbeat information 342. When the heartbeat information 326 and the reference heartbeat information 342 are within a defined threshold, the unlock module 330 can determine that the heartbeat information 326 matches the reference heart rate information 342 and the user is awake or conscious. Alternatively, when the heartbeat information 326 and the reference heartbeat information 342 are not within a defined threshold, the unlock module 330 can determine that the heartbeat information 326 does not match the reference heartbeat information 342 and the user is not awake or unconscious. Based on the heartbeat information 326 as well as the fingerprint information 312, the unlock module 330 can determine whether to unlock the electronic device 300 to allow the user to access the electronic device 300.

In one example, the unlock module 330 can compare the heartbeat information 326 of the user to the defined heartbeat range 332 and/or the reference heartbeat information 342 in order to determine whether the user is awake or conscious. In one example, if the user has a typical heart rate between 60-100 BPM and the user's heart rate is expected to be less when the user is sleeping, the unlock module 330 can compare the heartbeat information 326 to the defined heartbeat range 332 and not the reference heartbeat information 342. In another example, if the user does not fall under the typical heart rate of between 60-100 BPM or the user's heart rate is expected to still be within that range when the user is sleeping, the unlock module 330 may not compare the heartbeat information 326 to the defined heartbeat range 332, but rather to the reference heartbeat information 342 that is specific to the user. The unlock module 330 can analyze the heartbeat information 326 of the user accordingly such that false identifications of a user being awake or not awake based on the user's heartbeat interval or heart rate are minimized.

In one configuration, the electronic device 300 can provide one or more levels of access when the fingerprint information 312 of the user matches the predefined fingerprint information 352 stored in the data store 350 and/or the heartbeat information 326 indicates that the user's heartbeat interval or heart rate is within the defined heartbeat range 332 and/or the heartbeat information 326 matches the reference heart rate information 342. For example, the electronic device 300 can provide one of two levels of access based on the fingerprint information 312 and/or the heartbeat information 326. When the user wishes to access general files on the electronic device 300, the user can unlock the electronic device 300 by placing a finger on the sensor assembly of the electronic device 300 for a first period of time. When the user wishes to access more private files, the user can unlock the electronic device 300 by placing a finger on the sensor assembly for a second period of time that is longer than the first period of time so that the heartbeat information 326 can be captured using the heart rate sensor 320. When the user's heart rate is within a predefined range (e.g., a normal resting heart rate for that user), then the private files can be accessible, which can be useful for preventing access to private files. Therefore, in this example, a first level of access can be provided based on the fingerprint information 312, whereas a second level of access that encompasses more than the first level of access can be provided based on both the fingerprint information 312 and the heartbeat information 326.

In one example, the unlock module 330 can determine to keep the electronic device 300 locked to prevent access to the electronic device 300 when the fingerprint information 312 of the user does not match the predefined fingerprint information 352 stored in the data store 350 and/or or the heartbeat information 326 is not within the defined heartbeat range 332 or correspond with the reference heartbeat information 342 (which indicates that the user is not awake or unconscious). For example, when a fingerprint is a match but the heartbeat information 326 indicates that the user not awake or unconscious, the unlock module 330 can determine to keep the electronic device 300 locked in order to prevent an unauthorized access of the electronic device 300. In addition, when the heartbeat information 326 indicates that the user is awake or conscious but the fingerprint is not a match, the unlock module 330 can determine to keep the electronic device 300 locked in order to prevent an unauthorized access of the electronic device 300.

In one example, the unlock module 330 can determine to keep the electronic device 300 locked when no heartbeat information 326 is received. For example, if the unlock module 330 receives the fingerprint information 312 from the fingerprint sensor 310 but does not receive the heartbeat information 326 from the heart rate sensor 320, the unlock module 330 can determine to keep the electronic device 300 locked to prevent the user from accessing the electronic device 300.

In one example, the electronic device 300 can provide an audio or vibratory notification when an access to the electronic device 300 is not provided (e.g. denied) for the user (e.g., an access attempt has failed). The audio or vibratory notification can enable an authenticated user to become notified of a potentially fraudulent or deceitful attempt to gain access to the electronic device 300. In another example, the electronic device 300 can provide a textual notification for display that indicates an attempt to access the electronic device 300 has been denied. In this example, when the authenticated user successfully unlocks the electronic device 300, the user can become notified of the unsuccessful attempt to access the electronic device 300. Such a notification can be made on the device to which access was denied, or can be sent to another of the user's devices. In the first instance, the user can become notified of the failed authorization attempt the very next time that they access the device. Alternatively, notification to a different device can be made upon denial of access and the user can be made aware of the unauthorized access attempt the next time the user accesses this device. In one specific example, if access to a first device is attempted and denied, notification of the failed attempt can be immediately transmitted to a second device. In this way, the user may become aware of the attempt to access the first device in real time and can take mitigation action. For example, a child may attempt to gain unauthorized access to a parent's laptop in one room and the parent can receive a notification of the failed access attempt on their smartphone in another room. The parent can then take action to confront the child about the unauthorized access attempt. In some examples, a failed access may not be reported if followed by successful access within a specified short period of time. This can avoid generation of annoying meaningless notifications if a user's bona fide attempt to access their device fails for some reason. In some examples, the period of time can be less than 60 seconds, 30 seconds, or 10 seconds. In some examples, the exact duration of time can be set by the user.

Figure 4:
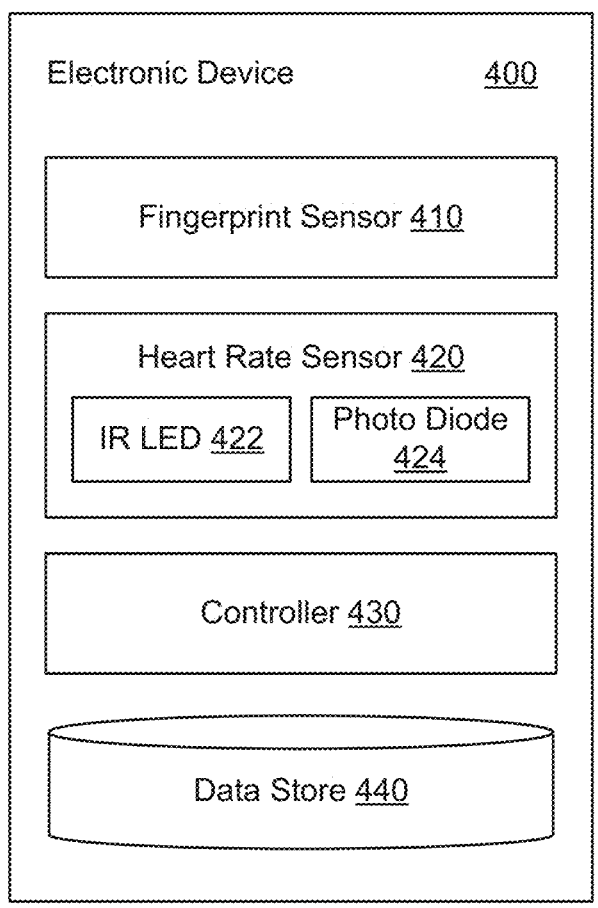
FIG. 4 illustrates an electronic device in accordance with an example embodiment.

FIG. 4 illustrates an example of an electronic device 400. The electronic device 400 can include a fingerprint sensor 410, a heart rate sensor 420 that includes an IR LED 422 and a photo diode 424, a controller 430 coupled to the fingerprint sensor 410 and the heart rate sensor 420, and a data store 440. The controller 430 can receive a fingerprint of a user captured using the fingerprint sensor 410. The controller 430 can determine whether the fingerprint of the user matches a predefined fingerprint stored in the data store 440 of the electronic device 400. The controller 430 can receive heart rate information of the user captured using the heart rate sensor 420. The controller 430 can determine whether the heart rate information is within a defined range. The controller 430 can unlock the electronic device 400 to allow the user to access the electronic device 400 when the fingerprint of the user matches the predefined fingerprint stored in the data store 440 and the heart rate information is within the defined range.

Figure 5:
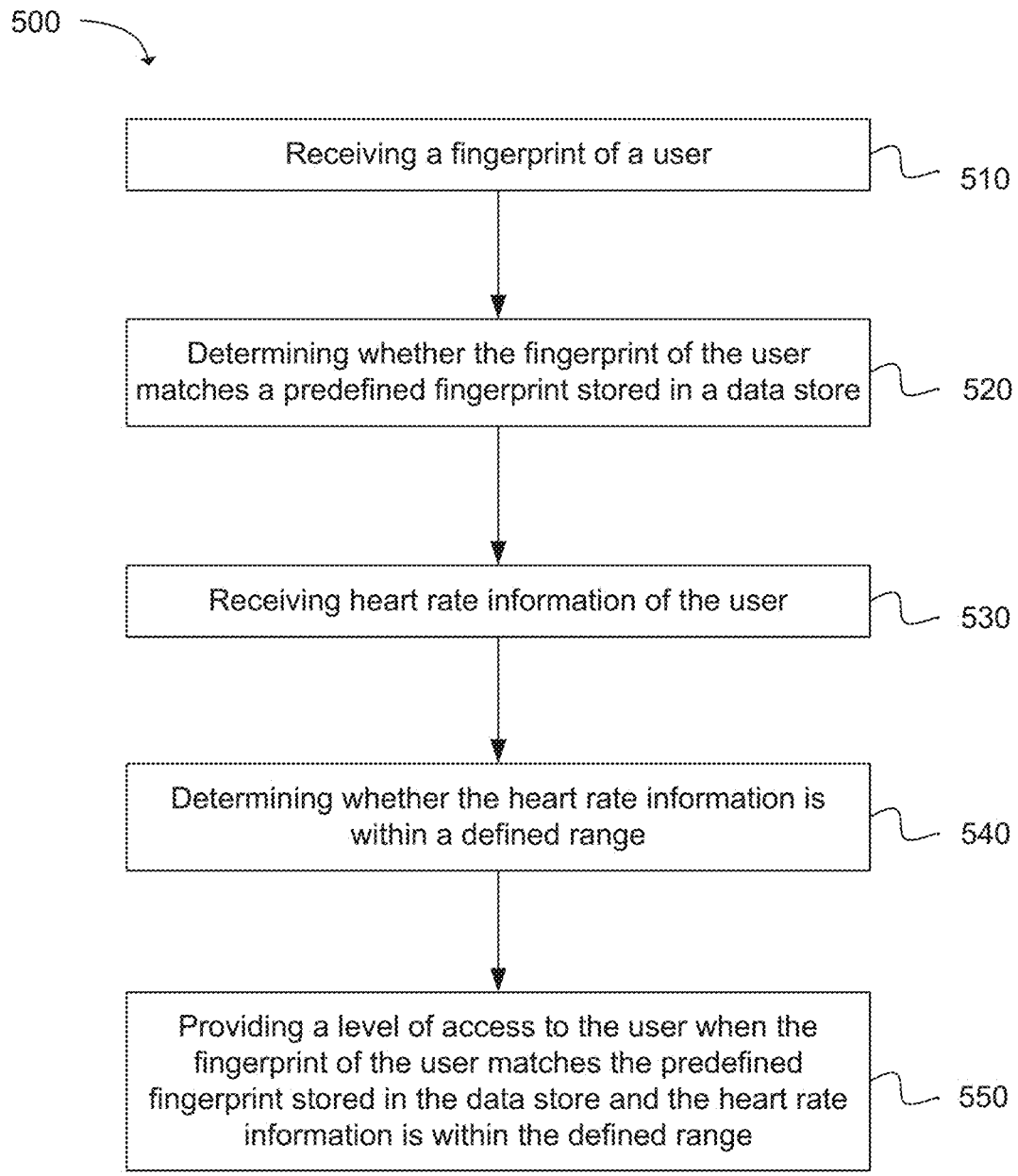
FIG. 5 is a flowchart illustrating operations for determining whether to provide access to an electronic device in accordance with an example embodiment.

Another example provides a method 500 for determining whether to provide access to an electronic device, as shown in the flow chart in FIG. 5. The method can be executed as instructions on a machine, where the instructions are included on at least one computer readable medium or one non-transitory machine readable storage medium. The method can include the operation of receiving a fingerprint of a user, as in block 510. The method can include the operation of determining whether the fingerprint of the user matches a predefined fingerprint stored in a data store, as in block 520. The method can include the operation of receiving heart rate information of the user, as in block 530. The method can include the operation of determining whether the heart rate information is within a defined range, as in block 540. The method can include the operation of providing a level of access to the user when the fingerprint of the user matches the predefined fingerprint stored in the data store and the heart rate information is within the defined range, as in block 550.

Figure 6:
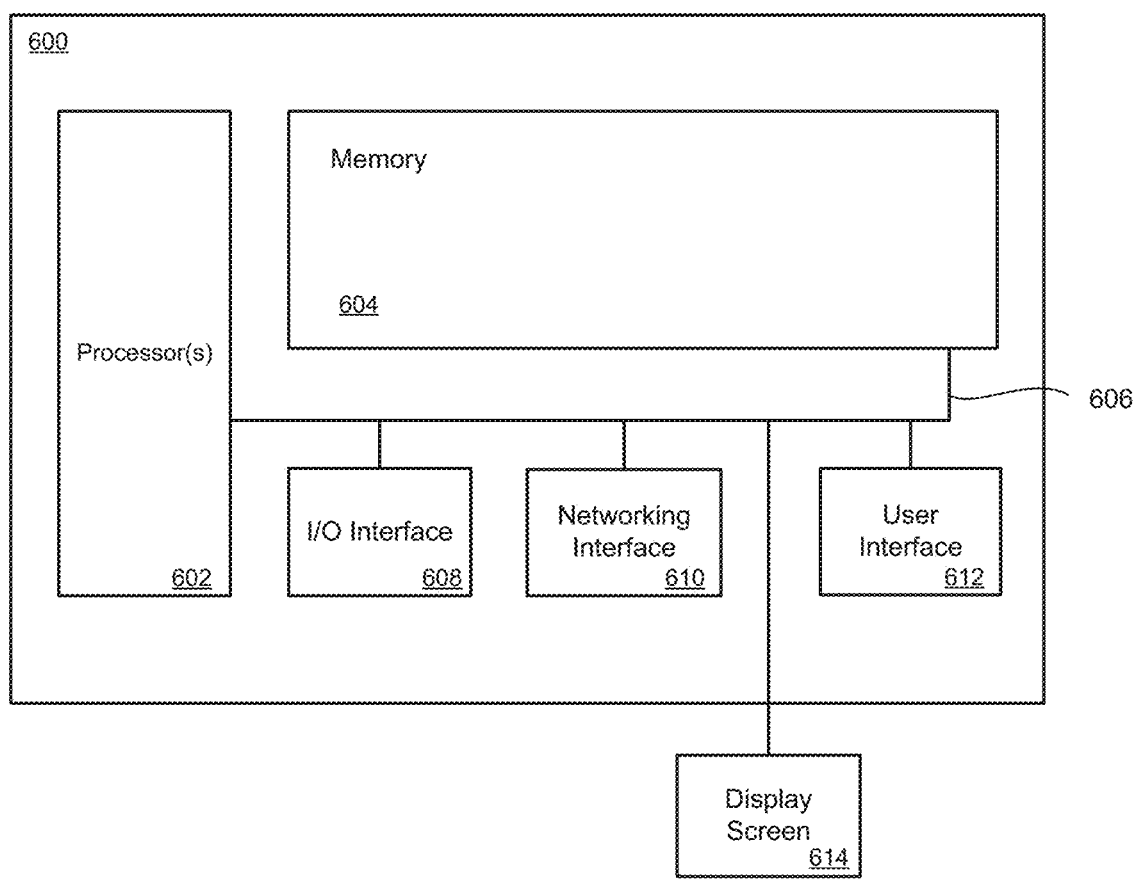
FIG. 6 illustrates a computing system that includes a data storage device in accordance with an example embodiment.

FIG. 6 illustrates a general computing system or device 600 that can be employed in the present technology. The computing system 600 can include a processor 602 in communication with a memory 604. The memory 604 can include any device, combination of devices, circuitry, and the like that is capable of storing, accessing, organizing, and/or retrieving data. Non-limiting examples include SANs (Storage Area Network), cloud storage networks, volatile or non-volatile RAM, phase change memory, optical media, hard-drive type media, and the like, including combinations thereof.

The computing system or device 600 additionally includes a local communication interface 606 for connectivity between the various components of the system. For example, the local communication interface 606 can be a local data bus and/or any related address or control busses as may be desired.

The computing system or device 600 can also include an I/O (input/output) interface 608 for controlling the I/O functions of the system, as well as for I/O connectivity to devices outside of the computing system 600. A network interface 610 can also be included for network connectivity. The network interface 610 can control network communications both within the system and outside of the system. The network interface can include a wired interface, a wireless interface, a Bluetooth interface, optical interface, and the like, including appropriate combinations thereof. Furthermore, the computing system 600 can additionally include a user interface 612, a display device 614, as well as various other components that would be beneficial for such a system.

The processor 602 can be a single or multiple processors, and the memory 604 can be a single or multiple memories. The local communication interface 606 can be used as a pathway to facilitate communication between any of a single processor, multiple processors, a single memory, multiple memories, the various interfaces, and the like, in any useful combination.

Various techniques, or certain aspects or portions thereof, can take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a RAM, EPROM, flash drive, optical drive, magnetic hard drive, solid state drive, or other medium for storing electronic data. The node and wireless device can also include a transceiver module, a counter module, a processing module, and/or a clock module or timer module. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations. Exemplary systems or devices can include without limitation, laptop computers, tablet computers, desktop computers, smart phones, computer terminals and servers, storage databases, and other electronics which utilize circuitry and programmable memory, such as household appliances, smart televisions, digital video disc (DVD) players, heating, ventilating, and air conditioning (HVAC) controllers, light switches, and the like.

Examples

The following examples pertain to specific technology embodiments and point out specific features, elements, or steps that can be used or otherwise combined in achieving such embodiments.

In one example, there is provided a controller in an electronic device. The controller can include logic to receive a fingerprint of a user. The controller can include logic to determine whether the fingerprint of the user matches a predefined fingerprint stored in a data store. The controller can include logic to receive heart rate information of the user. The controller can include logic to determine whether the heart rate information is within a defined range. The controller can include logic to provide access to the electronic device for the user matches the predefined fingerprint stored in the data store and the heart rate information is within the defined range.

In one example of the controller, the controller can include logic to determine that the user is conscious when the heart rate information is within the defined range.

In one example of the controller, the controller can include logic to determine that the heart rate information is within the defined range when a heart rate or a heart rate interval of the user included within the heart rate information is within the defined range.

In one example of the controller, the controller can include logic to: receive heart rate information of the user during an initial calibration period, wherein the heart rate information includes a reference heart rate or heart rate interval of the user when the user is conscious; and determine that the heart rate information indicates that the user is conscious when a heart rate or a heart rate interval included in the heart rate information corresponds to the reference heart rate or heart rate interval of the user when the user is conscious.

In one example of the controller, the controller can include logic to determine to not provide the access to the electronic device for the user when the fingerprint of the user does not match the predefined fingerprint stored in the data store or the heart rate information is not within the defined range, thereby indicating that the user is not conscious.

In one example of the controller, the controller can include logic to: cause the electronic device to provide an audio or vibratory notification when the access to the electronic device is not provided for the user; or provide a textual notification for display that indicates an attempt to access the electronic device has been denied.

In one example of the controller, the controller can include logic to determine to not provide the access to the electronic device for the user when no heart rate information is received.

In one example of the controller, the controller can include logic to receive updated heart rate information of the user during a recalibration period, wherein the updated heart rate information includes an updated reference heart rate or heart rate interval of the user when the user is conscious.

In one example of the controller, the controller can include logic to receive the fingerprint of the user from a fingerprint sensor.

In one example of the controller, the controller can include logic to receive the heart rate information from a heart rate sensor.

In one example of the controller, the controller is integrated with an electronic device, and the access provided to the user enables the user to access the electronic device.

In one example, there is provided an electronic device. The electronic device can include a fingerprint sensor, a heart rate sensor, and logic communicatively coupled to the fingerprint sensor and the heart rate sensor. The logic can be configured to receive a fingerprint of a user captured using the fingerprint sensor. The logic can be configured to determine whether the fingerprint of the user matches a predefined fingerprint stored in a data store of the electronic device. The logic can be configured to receive heart rate information of the user captured using the heart rate sensor. The logic can be configured to determine whether the heart rate information is within a defined range. The logic can be configured to unlock the electronic device to allow the user to access the electronic device when the fingerprint of the user matches the predefined fingerprint stored in the data store and the heart rate information is within the defined range.

In one example of the electronic device, the logic can be configured to determine that the user is conscious when the heart rate information is within the defined range.

In one example of the electronic device, the logic can be configured to determine that the heart rate information is within the defined range when a heart rate or a heart rate interval of the user included within the heart rate information is within the defined range.

In one example of the electronic device, the logic can be configured to: receive heart rate information of the user during an initial calibration of the electronic device, wherein the heart rate information includes a reference heart rate or heart rate interval of the user when the user is conscious; and determine that the heart rate information indicates that the user is conscious when a heart rate or a heart rate interval included in the heart rate information corresponds to the reference heart rate or heart rate interval of the user when the user is conscious.

In one example of the electronic device, the logic can be configured to keep the electronic device locked to prevent the user from accessing the electronic device when the fingerprint of the user does not match the predefined fingerprint stored in the data store or the heart rate information is not within the defined range, thereby indicating that the user is not conscious.

In one example of the electronic device, the logic can be configured to: provide an audio or vibratory notification when the access to the electronic device is not provided for the user; or provide a textual notification for display that indicates an attempt to access the electronic device has been denied.

In one example of the electronic device, the logic can be configured to keep the electronic device locked to prevent the user to access the electronic device when no heart rate information is received.

In one example of the electronic device, the logic can be configured to receive updated heart rate information of the user during a recalibration period, wherein the updated heart rate information includes an updated reference heart rate or heart rate interval of the user when the user is conscious.

In one example of the electronic device, the heart rate sensor includes an infrared light emitting diode (LED) and a photo diode to detect the heart rate information of the user.

In one example, there is provided a system that includes a data store, a fingerprint sensor, a heart rate sensor, an electronic device, and a controller. The controller can receive a fingerprint of a user captured using the fingerprint sensor. The controller can determine whether the fingerprint of the user matches a predefined fingerprint stored in the data store. The controller can receive heart rate information of the user captured using the heart rate sensor. The controller can determine whether the heart rate information is within a defined range. The controller can unlock the electronic device to allow the user to access the electronic device when the fingerprint of the user matches the predefined fingerprint stored in the data store and the heart rate information is within the defined range.

In one example of the system, the controller comprises logic to determine that the user is conscious when the heart rate information is within the defined range.

In one example of the system, the controller comprises logic to determine that the heart rate information is within the defined range when a heart rate or a heart rate interval of the user included within the heart rate information is within the defined range.

In one example of the system, the controller comprises logic to: receive heart rate information of the user during an initial calibration of the electronic device, wherein the heart rate information includes a reference heart rate or heart rate interval of the user when the user is conscious; and determine that the heart rate information indicates that the user is conscious when a heart rate or a heart rate interval included in the heart rate information corresponds to the reference heart rate or heart rate interval of the user when the user is conscious.

In one example of the system, the controller comprises logic to keep the electronic device locked to prevent the user from accessing the electronic device when the fingerprint of the user does not match the predefined fingerprint stored in the data store or the heart rate information is not within the defined range, thereby indicating that the user is not conscious.

In one example of the system, the controller comprises logic to: cause the electronic device to provide an audio or vibratory notification when the access to the electronic device is not provided for the user; or provide a textual notification for display that indicates an attempt to access the electronic device has been denied.

In one example of the system, the controller comprises logic to keep the electronic device locked to prevent the user from accessing the electronic device when no heart rate information is received.

In one example of the system, the controller comprises logic to receive updated heart rate information of the user during a recalibration period, wherein the updated heart rate information includes an updated reference heart rate or heart rate interval of the user when the user is conscious.

In one example of the system, the heart rate sensor includes an infrared light emitting diode (LED) and a photo diode to detect the heart rate information of the user.

In one example, there is provided a method of making an electronic device. The method can include providing a fingerprint sensor. The method can include providing a heart rate sensor. The method can include providing a controller that is communicatively coupled to the fingerprint sensor and the heart rate sensor. The method can include configuring the controller to perform the following: receiving a fingerprint of a user captured using the fingerprint sensor; determining whether the fingerprint of the user matches a predefined fingerprint stored in a data store of the electronic device; receiving heart rate information of the user captured using the heart rate sensor; determining whether the heart rate information is within a defined range; and unlocking the electronic device to allow the user to access the electronic device when the fingerprint of the user matches the predefined fingerprint stored in the data store and the heart rate information is within the defined range.

In one example of the method of making the electronic device, the method can include configuring the controller to perform the following: determining that the user is conscious when the heart rate information is within the defined range.

In one example of the method of making the electronic device, the method can include configuring the controller to perform the following: determining that the heart rate information is within the defined range when a heart rate or a heart rate interval of the user included within the heart rate information is within the defined range.

In one example of the method of making the electronic device, the method can include configuring the controller to perform the following: receiving heart rate information of the user during an initial calibration of the electronic device, wherein the heart rate information includes a reference heart rate or heart rate interval of the user when the user is conscious; and determining that the heart rate information indicates that the user is conscious when a heart rate or a heart rate interval included in the heart rate information corresponds to the reference heart rate or heart rate interval of the user when the user is conscious.

In one example of the method of making the electronic device, the method can include configuring the controller to perform the following: keeping the electronic device locked to prevent the user from accessing the electronic device when the fingerprint of the user does not match the predefined fingerprint stored in the data store or the heart rate information is not within the defined range, thereby indicating that the user is not conscious.

In one example of the method of making the electronic device, the method can include configuring the controller to perform the following: keeping the electronic device locked to prevent the user from accessing the electronic device when no heart rate information is received.

In one example of the method of making the electronic device, the method can include configuring the controller to perform the following: receiving updated heart rate information of the user during a recalibration period, wherein the updated heart rate information includes an updated reference heart rate or heart rate interval of the user when the user is conscious.

In one example of the method of making the electronic device, the method can include providing the heart rate sensor to include an infrared light emitting diode (LED) and a photo diode for detecting the heart rate information of the user.

In one example, there is provided at least one non-transitory machine readable storage medium having instructions embodied thereon. The instructions when executed by a controller performs the following: receiving a fingerprint of a user; determining whether the fingerprint of the user matches a predefined fingerprint stored in a data store; receiving heart rate information of the user; determining whether the heart rate information is within a defined range;

and providing access to an electronic device to the user when the fingerprint of the user matches the predefined fingerprint stored in the data store and the heart rate information is within the defined range.

In one example of the at least one non-transitory machine readable storage medium, the non-transitory machine readable storage medium further comprises instructions when executed perform the following: determining that the user is conscious when the heart rate information is within the defined range.

In one example of the at least one non-transitory machine readable storage medium, the non-transitory machine readable storage medium further comprises instructions when executed perform the following: determining that the heart rate information is within the defined range when a heart rate or a heart rate interval of the user included within the heart rate information is within the defined range.

In one example of the at least one non-transitory machine readable storage medium, the non-transitory machine readable storage medium further comprises instructions when executed perform the following: receiving heart rate information of the user during an initial calibration of the electronic device, wherein the heart rate information includes a reference heart rate or heart rate interval of the user when the user is conscious; and determining that the heart rate information indicates that the user is conscious when a heart rate or a heart rate interval included in the heart rate information corresponds to the reference heart rate or heart rate interval of the user when the user is conscious.

In one example of the at least one non-transitory machine readable storage medium, the non-transitory machine readable storage medium further comprises instructions when executed perform the following: determining to not provide the access to the user when the fingerprint of the user does not match the predefined fingerprint stored in the data store or the heart rate information is not within the defined range, thereby indicating that the user is not conscious.

In one example of the at least one non-transitory machine readable storage medium, the non-transitory machine readable storage medium further comprises instructions when executed perform the following: determining to not provide the access to the user when no heart rate information is received.

In one example of the at least one non-transitory machine readable storage medium, the non-transitory machine readable storage medium further comprises instructions when executed perform the following: receiving updated heart rate information of the user during a recalibration period, wherein the updated heart rate information includes an updated reference heart rate or heart rate interval of the user when the user is conscious.

In one example of the at least one non-transitory machine readable storage medium, the non-transitory machine readable storage medium further comprises instructions when executed perform the following: receiving the fingerprint of the user from a fingerprint sensor.

In one example of the at least one non-transitory machine readable storage medium, the non-transitory machine readable storage medium further comprises instructions when executed perform the following: receiving the heart rate information from a heart rate sensor.

In one example, there is provided a method of providing access to an electronic device. The method can include receiving a fingerprint of a user. The method can include determining whether the fingerprint of the user matches a predefined fingerprint stored in a data store. The method can include receiving heart rate information of the user. The method can include determining whether the heart rate information is within a defined range. The method can include providing access to the electronic device for the user when the fingerprint of the user matches the predefined fingerprint stored in the data store and the heart rate information is within the defined range.

In one example of the method of providing access to the electronic device, the method can further include determining that the user is conscious when the heart rate information is within the defined range.

In one example of the method of providing access to the electronic device, the method can further include determining that the heart rate information is within the defined range when a heart rate or a heart rate interval of the user included within the heart rate information is within the defined range.

In one example of the method of providing access to the electronic device, the method can further include: receiving heart rate information of the user during an initial calibration period, wherein the heart rate information includes a reference heart rate or heart rate interval of the user when the user is conscious; and determining that the heart rate information indicates that the user is conscious when a heart rate or a heart rate interval included in the heart rate information corresponds to the reference heart rate or heart rate interval of the user when the user is conscious.

In one example of the method of providing access to the electronic device, the method can further include comprising determining to not provide the access to the user when the fingerprint of the user does not match the predefined fingerprint stored in the data store or the heart rate information is not within the defined range, thereby indicating that the user is not conscious.

In one example of the method of providing access to the electronic device, the method can further include determining to not provide the access to the user when no heart rate information is received.

In one example of the method of providing access to the electronic device, the method can further include receiving updated heart rate information of the user during a recalibration period, wherein the updated heart rate information includes an updated reference heart rate or heart rate interval of the user when the user is conscious.

While the forgoing examples are illustrative of the principles of invention embodiments in one or more particular applications, it will be apparent to those of ordinary skill in the art that numerous modifications in form, usage and details of implementation can be made without the exercise of inventive faculty, and without departing from the principles and concepts of the disclosure.

What is claimed is:

1. A controller in an electronic device, the controller comprising:
   interface circuitry; and
   logic to:
   determine whether user fingerprint data matches reference fingerprint data, the user fingerprint data collected from a user via a fingerprint sensor;
   provide user access to first information on the electronic device in response to the user fingerprint data matching the reference fingerprint data;
   determine whether user heart rate information is within a heart rate range, the user heart rate information collected from the user via a heart rate sensor; and
   provide user access to second information on the electronic device in response to the user fingerprint data matching the reference fingerprint data and the user heart rate information being within the heart rate range, the second information more private than the first information.

2. The controller of claim 1, wherein the logic is to determine that the user is conscious in response to the user heart rate information being within the heart rate range.

3. The controller of claim 1, wherein the user heart rate information includes heart rate data or heart rate interval data for the user and the logic is to determine that the user heart rate information is within the heart rate range in response to the heart rate data or the heart rate interval data of the user being within the heart rate range.

4. The controller of claim 1, wherein the user heart rate information includes heart rate data or heart rate interval data for the user and the logic is to
determine that the user is conscious in response to the heart rate data or the heart rate interval data corresponding to reference heart rate data or reference heart rate interval data for the user when the user is conscious.

5. The controller of claim 1, wherein the logic is to maintain the electronic device in a locked state if the user fingerprint data does not match the reference fingerprint data.

6. The controller of claim 5, wherein the logic is to
cause the electronic device to output one or more of an audio notification, a vibratory notification, or a textual notification in response to the user access to the first information on the electronic device being denied.

7. The controller of claim 1, wherein the logic is to confirm whether the user heart rate information is within the heart rate range in response to receipt of updated heart rate information for the user.

8. An electronic device, comprising:
a fingerprint sensor to collect user fingerprint data from a user;
a heart rate sensor to collect user heart rate information from the user; and
a controller communicatively coupled to the fingerprint sensor and the heart rate sensor, the controller to:
determine whether the user fingerprint data matches reference fingerprint data;
provide user access to first information on the electronic device in response to the user fingerprint data matching the reference fingerprint data;
determine whether the user heart rate information is within a heart rate range; and
provide user access to second information on the electronic device in response to the user fingerprint data matching the reference fingerprint data and the user heart rate information being within the heart rate range, the second information more private than the first information.

9. The electronic device of claim 8, wherein the controller is to determine that the user is conscious in response to the user heart rate information being within the heart rate range.

10. The electronic device of claim 8, wherein the user heart rate information includes heart rate data or heart rate interval data for the user and the controller is to determine that the user heart rate information is within the heart rate range in response to the heart rate data or the heart rate interval data of the user being within the heart rate range.

11. The electronic device of claim 8, wherein the user heart rate information includes heart rate data or heart rate interval data for the user and the controller is to
determine that the user is conscious in response to the heart rate data or the heart rate interval data for the user corresponding to reference heart rate data or reference heart rate interval data for the user when the user is conscious.

12. The electronic device of claim 8, wherein the controller is to maintain the electronic device in a locked state to prevent the user from accessing the first information and the second information on the electronic device if the user fingerprint data does not match the reference fingerprint data.

13. The electronic device of claim 12, wherein the controller is to
generate one or more of an audio notification, a vibratory notification, or a textual notification in response to the user access to the first information on the electronic device being denied, the one or more of the audio notification, the vibratory notification, or the textual notification to be presented via one or more of the electronic device or a second user device.

14. The electronic device of claim 8, wherein the controller is to confirm whether the user heart rate information is within the heart rate range in response to receipt of updated heart rate information for the user.

15. The electronic device of claim 8, wherein the heart rate sensor includes an infrared light emitting diode (LED) and a photo diode to detect the user heart rate information.

16. A system, comprising:
a fingerprint sensor to collect user fingerprint data from a user;
a heart rate sensor to collect user heart rate information from the user; and
an electronic device, the electronic device including memory and a controller to:
determine whether the user fingerprint data matches reference fingerprint data;
provide user access to first information on the electronic device in response to the user fingerprint data matching the reference fingerprint data;
determine whether the user heart rate information is within a heart rate range; and
provide user access to second information on the electronic device in response to the user fingerprint data matching the reference fingerprint data and the user heart rate information being within the heart rate range, the second information more private than the first information.

17. The system of claim 16, wherein the controller is to determine that the user is conscious in response to the user heart rate information being within the heart rate range.

18. The system of claim 16, wherein the user heart rate information includes heart rate data or heart rate interval data for the user and the controller is to determine that the user heart rate information is within the heart rate range in response to the heart rate data or the heart rate interval data for the user being within the heart rate range.

19. The system of claim 16, wherein the user heart rate information includes heart rate data or heart rate interval data for the user and the controller is to
determine that the user is conscious in response to the heart rate data or the heart rate interval data for the user corresponding to reference heart rate data or reference heart rate interval data for the user when the user is conscious.

20. The system of claim 16, wherein the controller is to maintain the electronic device in a locked state to prevent the user from accessing the first information and the second information on the electronic device if the user fingerprint data does not match the reference fingerprint data.

21. The system of claim 20, wherein the controller is to cause the electronic device to output one or more of an audio notification, a vibratory notification, or a textual notification in response to the user access to the first information on the electronic device being denied.

22. The system of claim 16, wherein the controller is to confirm whether the user heart rate information is within the heart rate range in response to receipt of updated heart rate information for the user.

23. The system of claim 16, wherein the heart rate sensor includes an infrared light emitting diode (LED) and a photo diode to detect the user heart rate information.

24. The controller of claim 6, wherein the textual notification is to indicate that an attempt to access the electronic device has been denied.

25. The controller of claim 6, wherein the user fingerprint data is first user fingerprint data and the logic is to transmit the textual notification for presentation via a second user device if second user fingerprint data does not match the reference fingerprint data, the second user fingerprint data collected from the user after the first user fingerprint data.

26. The electronic device of claim 15, wherein the user heart rate information is associated with an amount of infrared light absorbed in response to a blood volume inside a fingertip of the user.

27. The system of claim 21, wherein the user fingerprint data is first user fingerprint data and the controller is to transmit the textual notification to a second user device if second user fingerprint data does not match the reference fingerprint data, the second user fingerprint data collected from the user after the first user fingerprint data.

28. The system of claim 23, wherein the user heart rate information is associated with an amount of infrared light absorbed in response to blood volume inside a fingertip of the user.

* * * * *